(12) United States Patent
Zappini et al.

(10) Patent No.: US 7,278,849 B2
(45) Date of Patent: Oct. 9, 2007

(54) DENTAL PROSTHESIS WITH METAL-FREE ANCHORING ELEMENTS

(75) Inventors: Gianluca Zappini, Torbole sul Garda (IT); Gerhard Zanghellini, Schaan (LI); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 473 days.

(21) Appl. No.: 10/640,135

(22) Filed: Aug. 13, 2003

(65) Prior Publication Data

US 2004/0038182 A1 Feb. 26, 2004

(30) Foreign Application Priority Data

Aug. 23, 2002 (DE) .................. 102 38 833

(51) Int. Cl.
*A61C 13/225* (2006.01)
(52) U.S. Cl. ........................ 433/178; 433/177
(58) Field of Classification Search ............... 433/178
See application file for complete search history.

(56) References Cited

U.S. PATENT DOCUMENTS

| | | |
|---|---|---|
| 4,717,341 A | 1/1988 | Goldberg et al. |
| 4,894,012 A | 1/1990 | Goldberg et al. |
| 5,062,799 A | 11/1991 | Duncan et al. |
| 5,098,304 A | 3/1992 | Scharf |
| 5,176,951 A | 1/1993 | Rudo |
| 5,679,299 A * | 10/1997 | Gilbert et al. .............. 264/103 |
| 5,759,029 A | 6/1998 | Toru et al. |
| 5,839,900 A | 11/1998 | Billet et al. |
| 6,799,969 B2 * | 10/2004 | Sun et al. .................... 433/167 |
| 2002/0025506 A1 | 2/2002 | Hagenbuch et al. |
| 2003/0054319 A1 * | 3/2003 | Gervais et al. ............. 433/173 |

FOREIGN PATENT DOCUMENTS

| | | |
|---|---|---|
| DE | 31 09 424 A1 | 10/1982 |
| DE | 88 11 589 | 11/1988 |
| DE | 38 21 091 A1 | 1/1989 |
| DE | 44 20 044 A | 12/1994 |
| DE | 198 18 210 C2 | 10/1999 |
| EP | 0 230 394 A2 | 7/1987 |
| EP | 0 389 552 B1 | 10/1990 |
| EP | 0 824 898 A2 | 2/1998 |
| EP | 1 138 272 A | 10/2001 |
| WO | WO 02/30647 A2 | 4/2002 |

OTHER PUBLICATIONS

Diamond, "Resin Fiberglass Bonder Retainer," JCO, XXI(3):182-183 (1987).
körber et al., "Zhantechnische Herstellung von ästhetisch-Funktionellen Brückenknostruktionen," *DSL*, pp. 12-14 (1996).

* cited by examiner

*Primary Examiner*—Cris Rodriguez
*Assistant Examiner*—Candice C. Stokes
(74) *Attorney, Agent, or Firm*—Nixon Peabody LLP

(57) ABSTRACT

The invention relates to dental prostheses which have at least one metal-free anchoring element made of plastic material with a bending modulus of elasticity of at least 10 GPa and a maximum elongation of at least 0.8%.

17 Claims, 1 Drawing Sheet

DENTAL PROSTHESIS WITH METAL-FREE ANCHORING ELEMENTS

Figure 1:
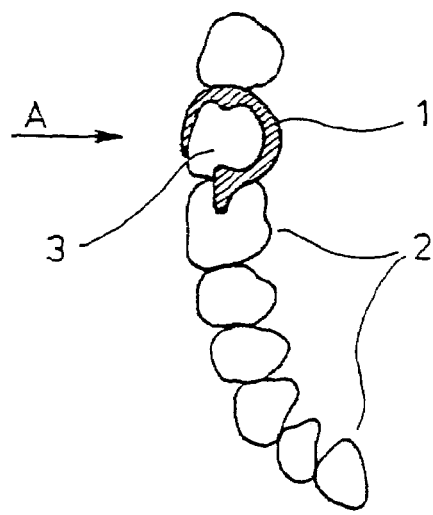

The invention relates to dental prostheses which have metal-free anchoring elements.

Metal-containing dental prostheses are increasingly being replaced by metal-free prostheses for aesthetic reasons. Composite materials which contain particle-shaped or fibrous fillers have proved suitable as materials for the preparation of metal-free prostheses.

EP 0 230 394 A2 discloses orthodontic apparatuses, such as e.g. tooth clasps, made of fibre-reinforced plastic which preferably takes the form of wires.

EP 0 389 552 B1 discloses temporary and permanent bridges based on fibre-reinforced plastics. In order to prepare the bridges, plastic teeth are secured to a strip made of glass-fibre-reinforced plastic and this is then fixed in the patient's mouth by adhesion to the teeth adjacent to the gap to be closed.

U.S. Pat. No. 5,098,304 describes the preparation of dental restorations based on glass-fibre-reinforced composite materials.

A two-stage process for the preparation of dental prostheses is known from U.S. Pat. No. 5,839,900 which comprises the preparation of a fibre-reinforced structure and the subsequent veneering of the structure with a composite material (cf. also K. H. Körber et al., DSL 3/96 12).

U.S. Pat. No. 5,062,799 discloses dental veneering materials which consist of glass-fibre material coated on both sides with composite material and are glued onto the tooth surface.

U.S. Pat. No. 5,176,951 relates to dental restorations which are reinforced with woven fabrics based on aramid or polyethylene fibres.

DE 38 21 091 A1 describes the preparation of dental prostheses with metal cast clasps in which a light-polymerizable resin preparation, which contains an ethylenically unsaturated compound and an organic filler, is shaped using a model into a clasp which, after curing, serves for the preparation of a casting mould for the preparation of the metal cast clasps according to the lost-wax process.

Monomer-free materials based on acetal resin are sold by Micro Dental Laboratories under the name Dental D® and are suitable for the preparation of metal-free dental prostheses and are intended to facilitate the preparation of partial prostheses with tooth-coloured anchoring elements.

For the same purpose and under the name Thermoflex®, Trident Dental Laboratories sells a material which is intended to have a monomer-free, crystalline structure and is also based on acetal resin.

Good results were achieved with plastics and composites in many dental applications. For example, crowns and bridges based on fibre-reinforced composites, which are veneered with glass-powder-containing plastics, are characterized by a high loading capacity, so that metal reinforcements can be dispensed with, without disadvantages. In other areas, however, the properties of metals could not be achieved to date with plastics. Thus, metal clasps are still the means of choice for securing partial prostheses to the patient's residual denture if a secure anchoring is the main priority. The reliability of metal clasps cannot be achieved by the use of clasps based on acetal resins. On the other hand, metal clasps are often relatively inflexible, which makes insertion and removal of the prosthesis difficult and carries the risk of damaging the anchoring teeth. In addition, the deforming of the clasp associated with the insertion and removal of the restoration readily leads to plastic deformations of the clasp and material fatigues due to the relatively low elasticity of metal clasps.

Accordingly, the object of the invention is to provide dental prostheses which can be easily inserted and removed again without damaging teeth and prosthesis and which can be securely anchored in the patient's mouth without the use of metals.

This object is achieved by dental prostheses which have at least one anchoring element made of plastic material which has a bending modulus of elasticity of at least 10 GPa and a maximum elongation of at least 0.8% before plastic deformation occurs. Anchoring elements made of plastic material with a bending modulus of elasticity of 10 to 80 GPa and a maximum elongation of 0.8 to 4% are preferred. As anchoring elements for dental prostheses often have a clasp-shaped appearance, they are also described in the following as clasps.

According to the invention, by dental prostheses is meant complete and preferably partial prostheses. Complete prostheses are referred to in the case of removable dentures which provide oral rehabilitation in the case of a completely toothless jaw. Complete prostheses can be secured to implants with anchoring elements. Partial prostheses or part prostheses are removable dentures for oral rehabilitation in the case of partial loss of teeth, which can be secured to the patient's residual denture and/or to suitable implants.

Partial prostheses can be broken down into various components. The actual denture is represented by the saddle(s). These are the restorations provided with artificial teeth, which rest against the toothless jaw sections in the region of an interrupted or shortened row of teeth. If a partial prosthesis contains several saddles, these are connected to each other by connecting elements. The saddles and their connecting elements together form the prosthesis base. In the case of prostheses with only one saddle, this is described as the base. The base of a partial prosthesis is not secured sufficiently firmly in the mouth by adhesion alone. It is therefore usually fixed to the residual denture or implants with anchoring elements. The dental prostheses according to the invention have a prosthesis base with at least one, usually 1 to 3 saddles and at least one anchoring element, usually 2 to 8 anchoring elements. As prostheses are always individual pieces which must be adapted to the patient's respective situation, no information can be given on the preferred number of saddles and anchoring elements.

The invention is based on the surprising finding that it is less the breaking strength of the material of the clasp and much more a balanced combination of bending modulus of elasticity and maximum elongation which is responsible for a secure anchoring of restorations in the patient's mouth. This combination of properties can be realized in particularly preferred manner by clasps made of plastic material which contains a polymeric matrix material into which a fibrous filler is embedded (fibre-reinforced plastic). The fibre-reinforced plastic is preferably veneered with a polymer material. The fibre-reinforced plastic is therefore also described in the following as core material. The veneering material contains no fibrous filler.

The plastic material, i.e. the core material or the combination of core and veneering material, has a bending modulus of elasticity of at least 10 GPa and preferably of 10 to 80 GPa, particularly preferably 10 to 50 GPa, and a maximum elongation of at least 0.8%, preferably of 0.8 to 4%, particularly preferably 2.0 to 3.5%. The bending modulus of elasticity of the clasp material is determined analogously to DIN/ISO 178. By the maximum elongation is meant the elongation which the material can withstand without plastic deformation and mechanical damage (e.g. breaking of a layer or its flaking off). This is also determined according to DIN/ISO 178.

Bending modulus of elasticity and maximum elongation are preferably chosen such that the flexibility of the material, which is defined as the quotient of maximum elongation in % and bending modulus of elasticity in GPa, is in the region of $0.4 \cdot 10^{-3}$ to $15 \cdot 10^{-3}$ GPa$^{-1}$, preferably $1 \cdot 10^{-3}$ to $5 \cdot 10^{-3}$ GPa$^{-1}$.

Bending modulus of elasticity and maximum elongation are substance constants which are characteristic of a given material. In the case of material combinations, such as combinations of core material and veneering material, various values for the bending modulus of elasticity and the maximum elongation can be given for the core and the veneering material. The values of the clasp material are determined by the values of the materials used to prepare the clasp and by their layer thicknesses. For example, a plastic material with a bending modulus of elasticity defined as above can be obtained by combining a relatively thick layer of a core material with relatively low bending modulus of elasticity with a relatively thin layer of veneering material, or else by combining a relatively thin layer of a core material with relatively high bending modulus of elasticity with a relatively thick layer of veneering material, it being assumed that the veneering material, which contains no fibrous filler, has a lower bending modulus of elasticity than the core material. Bending modulus of elasticity and maximum elongation are measured in each case using the clasp material, i.e. in the case of material combinations these are measured analogously to the mentioned DIN/ISO standards. In the case of clasps which consist exclusively of the core material, the clasp values are identical to the values of the core material.

According to the invention, the use of combinations of at least two plastics, i.e. of at least one core material and at least one veneering material, is preferred for the preparation of clasps as the veneering ensures that the fibres of the core material are protected against damage when the prosthesis is inserted and removed and thus an irritation of the gum caused by free fibre ends is prevented. In addition, a targeted setting of bending modulus of elasticity, elongation and flexibility is possible by the combination of core and veneering material. The use of veneering materials without inorganic fillers is preferred as more favourable values for flexibility can be achieved without inorganic fillers.

One or more, preferably 1 to 3 veneering materials can be used to veneer the core material. The colour of the clasp, for example, can be particularly well adapted to the adjacent natural teeth through the use of differently coloured veneering materials.

According to a preferred version, core materials are used with a bending modulus of elasticity of more than 20 GPa, particularly preferably 30 to 100 GPa, and a maximum elongation of more than 1%, particularly preferably 1.5 to 3.0%. The veneering materials preferably have a bending modulus of elasticity of 2 to 15 GPa, particularly preferably 2 to 5 GPa, and a maximum elongation of more than 1%, particularly preferably 2 to 5%.

Fibre-reinforced plastics, i.e. plastics which contain an organic, polymeric matrix, a fibrous filler embedded therein and if necessary a particulate filler, are used as core materials. The particulate filler can be of organic or inorganic nature. The core materials are obtained by the polymerization of suitable uncured starting materials which, in addition to a fibrous and if necessary particulate filler, contain a polymerizable binding agent and initiators for radical polymerization as well as if necessary further auxiliaries and additives. These starting materials are also described in the following as curable core materials.

The binding agents used in the invention contain at least one polymerizable monomer, oligomer and/or macromonomer. Oligomers are constructed of at least 5, usually of 50 to 300 monomer components.

Suitable monomers according to the invention are described e.g. in DE 198 18 210 C2, page 4. Preferred monofunctional monomers are methyl (meth)acrylate, isobutyl (meth)acrylate, butoxymethyl (meth)acrylate, 2-ethylhexyl (meth)acrylate, isodecyl (meth)acrylate, phenoxymethyl (meth)acrylate, ethyl (meth)acrylate, butyl (meth)acrylate, benzyl (meth)acrylate, phenyl (meth)acrylate and tetrahydrofurfuryl (meth)acrylate, cyclohexyl (meth)acrylate, hydroxyethyl (meth)acrylate (HEMA), glycerol mono(meth)acrylate. By monofunctional monomers is meant monomers with a radically polymerizable group.

According to a preferred version, the binding agent contains at least one monomer with two or more radically polymerizable groups. Such compounds act as cross-linkers during polymerization. Preferred monomers with two radically polymerizable groups are 1,4-butanediol di(meth)acrylate, 1,6-hexanediol di(meth)acrylate, 1,9-nonanediol di(meth)acrylate, decane methylene glycol dimethacrylate, bis-[4-(meth)acryloxy-2-hydroxypropyloxyphenyl]propane, polyethylene glycol (meth)acrylate (PEG (meth)acrylate), for example based on PEG 300, 400 or 1000, bisphenol-A di(meth)acrylate, in particular ethylene glycol di(meth)acrylate, triethylene glycol di(meth)acrylate, dipropylene glycol di(meth)acrylate, bis-GMA (2,2-bis-4-(3-(meth)acryloxy-2-hydroxypropyl)-phenylpropane), 1,1,6-trimethylhexamethylene urethane di(meth)acrylate, urethane di(meth)acrylate (UDMA, reaction product of hydroxyethyl (meth)acrylate or hydroxypropyl (meth)acrylate with 2,2,4-trimethylhexyl-1, 6-diisocyanate), glycerol di- and -tri(meth)acrylate.

Preferred monomers with more than two radically polymerizable groups are trimethylolpropane tri(meth)acrylate, pentaerythritol tetra(meth)acrylate and dipentaerythritol penta(meth)acrylate.

The corresponding methacrylate derivatives are particularly preferred in the case of all given monomers. Hydroxyethyl (meth)acrylates and glycerol di(meth)acrylates (GDMA) are quite particularly preferred.

Suitable as fibrous fillers are, particularly, ceramic fibres, organic fibres, such as aramid or polyethylene fibres, boron fibres, carbon fibres and in particular glass fibres. The fibrous fillers are preferably used in the form of long fibres. Core materials which contain 43 to 70 wt.-% fibrous filler are preferred. The fibres preferably have a diameter of 10 to 30 µm. By long fibres is meant fibres, the length of which is at least 500 times the diameter, preferably 1,000 to 10,000 times the diameter.

Suitable as particulate fillers are in particular quartz, glass ceramic or glass powder, aluminium and silicon oxide powder, powder based on silicate glasses, such as barium silicate, Li/Al-silicate glasses and barium glasses, as well as mixtures thereof. These fillers are used as powder with an average particle size of preferably 0.1 to 50 µm, in particular 1 to 20 µm.

Furthermore, the so-called composite fillers are also usable in the context of the invention, and can be obtained by polymerization of a mixture of one of the above-mentioned inorganic fillers and a binding agent, and subsequent grinding of the cured polymerisate.

In addition, the core material or its uncured starting material can contain pigments, preferably oxide based inorganic colouring pigments, X-ray opacity agents, preferably ytterbium fluoride, thixotropic agents, such as pyrogenic and/or precipitated silicic acids, accelerators, for example metal salts and complex compounds, such as copper acetate, copper acetylacetonate, copper salicylate, Co-EDTA complex, and further additives and auxiliaries. Silicic acids are usually used in an amount of up to 20 wt.-%, preferably 1 to 10 wt.-%, relative to the mass of the core material.

Suitable as polymerization initiators are all initiators of the radical polymerization, such as redox systems and initiators for light curing.

Preferred redox initiators (oxidizing substances) are cobaltic chloride, peroxides, such as tert.-butyl hydroperoxide, ferric chloride, perboric acid and its salts, permanganates and persulfate anions. Hydrogen peroxide can also be used. Quite particularly preferred initiators are benzoxyl peroxide (BPO) and lauroyl peroxide. When simultaneously using photoinitiators, interactions can occur with the above-mentioned oxidizing substances, so that photoinitiator and redox initiator should be matched to each other. The redox initiators can be used alone for curing the polymerizable materials or preferably in combination with activators.

Preferred activators (reducing substances) are amines, in particular diethanol-p-toluidine, ascorbic acid, barbituric acid derivatives, cobalt(II) chloride, ferrous chloride, ferrous sulfate, hydrazine, oxalic acid, thiocarbamide and salts of dithionite or sulfite anions. Quite particularly preferred activators are diethanol-p-toluidine, ascorbic acid and benzylphenyl barbituric acid (BPBA).

The most preferred redox system is BPO/BPBA.

Preferred photoinitiators are benzoin ethers, dialkyl benzil ketals, dialkoxy acetophenones, acylphosphine oxides, α-diketones, such as 9,10-phenanthrenequinone, diacetyl, furyl, anisil, 4,4'-dichlorobenzil, 4,4'-dialkoxy benzil and in particular camphorquinone. These photoinitiators can be used alone or in combination. Mixtures of photo- and redox initiators are also suitable.

Preferred amount ranges for the individual components of the core material or its uncured starting material, which can be chosen independently of each other, are:

25 to 52 wt.-%, preferably 25 to 40 wt.-%, particularly preferably 30 to 40 wt.-% polymerizable binding agent, 43 to 70 wt.-%, preferably 50 to 70 wt.-%, particularly preferably 55 to 65 wt.-% fibre-reinforced filler, 3 to 8 wt.-%, preferably 3 to 6 wt.-%, particularly preferably 3 to 4 wt.-% particulate filler, <2.5 wt.-%, preferably <1.5 wt.-%, particularly preferably 0.05 to 1.0 wt.-% initiator for radical polymerization, <2.5 wt.-%, preferably <2 wt.-%, particularly preferably 0.1 to 1.2 wt.-% stabilizer, and <0.3 wt.-%, preferably <0.1 wt.-%, particularly preferably 0.001 to 0.08 wt.-% pigments, in each case relative to the overall mass of the core material or of the uncured starting material.

Particularly preferred are materials which contain all components in the given preferred amounts.

A quite particularly preferred polymerizable core material has the following composition:

| Bis-GMA | 25.0-40.0 wt. % |
|---|---|
| Triethylene glycol dimethacrylate | 6.0-10.0 wt. % |
| Urethane dimethacrylate | <1.0 wt. % |
| Decane methylene glycol dimethacrylate | <1.0 wt. % |
| Highly dispersed silicon dioxide | 3.0-8.0 wt. % |
| Glass fibres, silanized | 43.0-70.0 wt. % |
| Catalysts and stabilizers | <0.5 wt. % |
| Pigments | <0.1 wt. % |

All percentages relate to the overall mass of the polymerizable core material.

According to a particularly preferred version, the fibrous filler is impregnated with the polymerizable matrix material, the initiator, if necessary the particulate filler and further components, and can thus be processed, i.e. moulded and cured, directly by the dentist or dental technician. These pre-impregnated materials preferably take the form of small rods or mats.

Preferably paste-like polymerizable materials, which contain a polymerizable binding agent, initiator for radical polymerization and if necessary filler, preferably organic filler, are used as veneering material. Veneering materials which are free from inorganic filler are particularly preferred. The veneering materials contain no fibrous filler. The above-mentioned materials, which are also used to prepare the core materials, are preferred as binding agents, initiators and if necessary fillers.

Suitable as organic fillers are, particularly, organic plastic particles, in particular precured plastic particles, i.e. partially polymerized particles which still have radically polymerizable groups. According to a particularly preferred version, these particles are based on the same monomers as the binding agent used to prepare the polymer material, so that filler and binding agent have essentially the same composition after the curing. In such cases, although the organic filler is visible in the photomicrograph of the cured polymer material, it has only a minor influence on the modulus of elasticity or the rigidity of the material and therefore acts as a non-reinforcing filler. The materials therefore have practically the same properties as materials which are prepared without filler. The use of such fillers serves primarily to set the viscosity and the polymerization shrinkage of the material.

Preferred amount ranges for the individual components of the veneering material, which can be chosen independently of each other, are:

50 to 80 wt.-%, preferably 50 to 70 wt.-%, particularly preferably 60 to 70 wt.-% organic filler, 20 to 50 wt.-%, preferably 30 to 50 wt.-%, particularly preferably 30 to 40 wt.-% polymerizable binding agent, <2 wt.-%, preferably <1.5 wt.-%, particularly preferably 0.1 to 1.0 wt.-% initiator for radical polymerization and 0 to 1 wt.-%, preferably 0.05 to 1.0 wt.-%, particularly preferably 0.1 to 0.7 wt.-% activator for radical polymerization, in each case relative to the overall mass of the veneering material.

Particularly preferred are veneering materials which contain all components in the given preferred amounts.

A quite particularly preferred veneering material based on inorganic fillers has the following composition:

| Bis-GMA | <10.0 wt. % |
|---|---|
| Urethane dimethacrylate | <10.0 wt. % |
| Decane methylene glycol dimethacrylate | <5.0 wt. % |
| Highly dispersed silicon dioxide | 5.0-20.0 wt. % |
| Barium glass filler, silanized | 35.0-60.0 wt. % |
| Mixed oxide, silanized | 15.0-25.0 wt. % |
| Catalysts and stabilizers | <1.0 wt. % |
| Pigments | <0.1 wt. % |

All percentages relate to the overall mass of the veneering material.

Filler-containing veneering materials are preferably prepared in the form of two components, a solid component and a liquid component, the solid component containing the organic filler and preferably the initiator for radical polymerization, and the liquid component containing the polymerizable binding agent and if necessary the activator for radical polymerization.

A particularly preferred two-component veneering material based on organic filler has the following composition:

| Powder component: | |
|---|---|
| PMMA | >98.0 wt. % |
| Benzoyl peroxide, pigments | <2.0 wt. % |
| Liquid component: | |
| Methyl methacrylate | 60.0-90.0 wt. % |
| Ethylene glycol dimethacrylate | 5.0-40.0 wt. % |
| Amine (diethanol-p-toluidine) | 0-1.0 wt. % |

The percentages relate in each case to the overall mass of the powdery or liquid component.

The curable matrix material and the curable veneering material can be cured by polymerization, preferably by radical polymerization.

Another object of the invention are kits for the preparation of dental prostheses. The kits according to the invention contain at least one curable core material, preferably 2 to 5 different core materials, e.g. differently shaped core materials, and at least one curable veneering material, preferably 1 to 5 different veneering materials, e.g. differently coloured core materials. In addition, the kit also preferably contains artificial teeth which can be arranged on the prosthesis base. Kits which contain core and veneering materials with the above-mentioned composition are particularly preferred.

The curable core materials are preferably used in the form of differently dimensioned small rods and mats in which the fibrous filler is impregnated with binding agent, initiator and if necessary the particulate filler, and which can be removed from the packaging, cut and shaped as required. Single-component core materials, that is, materials which can be cured directly, i.e. without adding a second component, for example by heat or light, are particularly preferred.

The measurement and design of the clasps is carried out in per se known manner (cf. e.g. Reinhard Marxkors, Lehrbuch der zahnärztlichen Prothetik [Textbook of dental prosthetics], 3rd edition, Deutscher Zahnärzte Verlag) and depends on the individual conditions of the respective mouth situation. In general, the anchoring elements according to the invention have a round to semicircular cross-section shape, by "semicircular" being meant also such cross-section shapes which more or less comprise a semicircle. The cross-section shapes of the clasps can be also derived from ellipsoidal surfaces, i.e. can also for example take the form of a semiellipse.

The object of the invention is also a process for the preparation of dental prostheses with metal-free anchoring elements, in which a prosthesis base is provided with anchoring elements made of a core material as defined above and the anchoring elements are then if necessary veneered with a veneering material and cured. The anchoring elements can be shaped simultaneously with the prosthesis base or subsequent to this. Core material and veneering material can be cured together after the shaping of the anchoring elements, for example by heating. Alternatively, the curing can take place successively, by initially curing the core material and then applying and curing the veneering material. When using more than one core material or more than one veneering material, the curing of the individual materials can take place layer-by-layer. The prosthesis is then completed in customary manner by attaching the dentures.

For aesthetic reasons, the clasp cross-sections preferably have a dimension of a maximum of 1 mm in the tooth horizontal. In order to guarantee the desired mechanical properties, the minimum dimension in horizontal direction is preferably 0.6 mm.

The dimensions of the clasp cross-section are preferably 1 to 2 mm in vertical direction, wherein the clasps can taper at the end and can be stronger in the region of the clasp base, i.e. in the region where they meet the prosthesis.

In the case of veneered anchoring elements, the thickness of the layer of the veneering material is preferably at least 0.1 mm, particularly preferably 0.1 to 0.2 mm.

The described materials, i.e. core and veneering materials, are particularly suitable for the preparation of anchoring elements of dental prostheses. In addition, they can advantageously also be used to prepare connecting elements, e.g. sublingual bars, but also to prepare the prosthesis saddles.

FIG. 1 shows a top view of the anchoring of a prosthesis to a natural tooth. The clasp 1 of the prosthesis 2 surrounds the anchoring tooth 3 in a horizontal plane. In order to guarantee a secure holding of the prosthesis, the clasp must rest securely against the tooth and must not allow any movement of the prosthesis.

Figure 2:
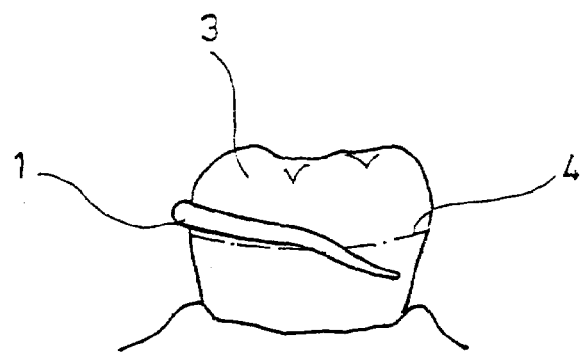

FIG. 2 shows a side view of the clasp (viewing direction A). The clasp 1 is arranged here such that it covers the tooth 3 below the tooth equator 4, i.e. the largest cross-section of the tooth. In this way, the prosthesis is secured against vertically acting tensile forces.

Figure 3:
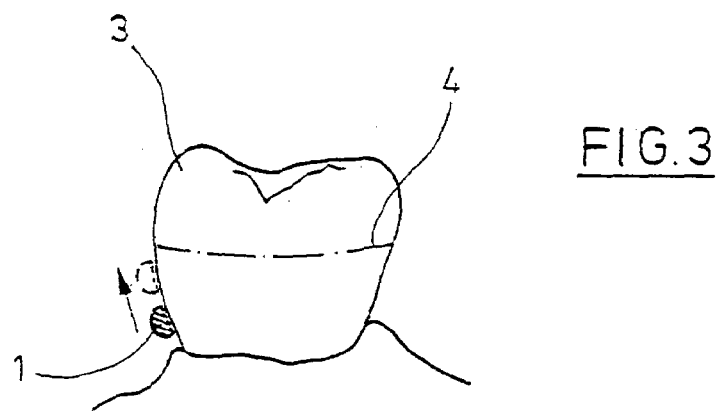

In order to remove the prosthesis, the clasp must be bent open in order that it can be guided over the equator 4 of the tooth 3 (FIG. 3). Even minor open bends can cause plastic deformations and fatigues of metal clasps. In contrast, the plastic clasps according to the invention are characterized by a high degree of elasticity, and can thus withstand considerably greater upward bends than metal clasps, without plastic deformation. Open bends of more than 1.5 mm can be achieved without any problems using the clasps according to the invention, which represents a considerable improvement compared with metal clasps which usually permit open bends of 0.2 to 0.6 mm.

The open or upward bend is measured on semicircular standard clasps with a radius of 4 mm which are formed from metal or plastic wire with a round cross-section and a diameter of 1 mm.

The maximum open bend is calculated, i.e. the maximum possible open bend without the clasp being irreversibly deformed or mechanically damaged.

The open bend is a measure of the geometric deformability of the clasps during insertion or removal. The greater the difference of the upward bend to the undercut, the safer the usage will be. This is also particularly advantageous if the prosthesis is canted during insertion or otherwise, as the risk of damage to the clasp is clearly reduced.

In prosthetics, the undercut is described as the geometric difference between the equator of a tooth (maximum diameter) and the support region of the clasp.

On the other hand, the clasps according to the invention have a clearly greater strength than the known acetal clasps and thus guarantee a much more secure fit of the prosthesis than these, such that advantageously the positive properties of metal and acetal clasps can be jointly realized.

Treating a partially edentulous arch using a partial prosthesis begins with the preparation of the base. After preparing the residual denture (fillings, periodontal treatment), diagnostic models are created on which the dentist sketches a design of the base after measuring. It is often necessary with the teeth intended for this to create space to house occlusal rests by preparing small cavities, in order to prevent the occlusion being disrupted by the support.

After a further diagnostic impression is taken and a model is prepared, the final drawing in of the design of the base is carried out and it is prepared in the laboratory. The base is checked in the patient to ensure that it fits perfectly. For arrangement of the artificial teeth which now follows, the models must be mounted in the articulator through a bite registration, the base advantageously being used as a bite wafer, after it has been provided with a wax rim in the region of the saddle(s). After trying out the base with the teeth arranged in wax, the prosthesis is completed and incorporated. Several prosthesis saddles are connected to each other by plastic bars.

The prosthesis base is preferably also prepared without the use of metals. A preferred material for this is polymethyl (meth)acrylate (PMMA), into which the dentures and the anchoring elements are inserted. The dentures are preferably also based on PMMA. According to a further, preferred version, the preparation of the prosthesis base, i.e. the saddles and connecting elements, is carried out using the above-described core and veneering materials, the veneering materials preferably being gum-coloured.

The prostheses or prosthesis parts according to the invention have the necessary strength for the chewing load, but also the required flexibility for the daily changing of the prosthesis. It was found that fixing elements made of fibre-reinforced composite material enable a secure fixing of partial prostheses without having the disadvantages of metal or acetal clasps. The dental prostheses according to the invention therefore have a combination of properties which guarantees high application safety for the desired purpose and represents an unexpected improvement compared with the state of the art.

The invention is described in the following with reference to embodiments.

EXAMPLES

Example 1

Determination of the Mechanical Properties of Testpieces

In order to determine the mechanical properties of the examined materials, rod-shaped testpieces with a width of 4 mm were prepared. Unless otherwise stated, the overall thickness was 1.05 mm. Testpieces made of veneered, fibre-reinforced plastics consisted of core material which was coated with polymer material on the upper side and underside. The thickness of the layer of the fibre-filled core material was 0.75 mm, the thickness of the veneering layers in each case 0.15 mm.

The bending modulus of elasticity and the maximum elongation were measured according to DIN/ISO 178. The results are shown in Table 1. The open or upward bend also listed was measured on semicircular standard clasps with a clasp radius of 4 mm and a material diameter of the clasp arm of 1 mm. The maximum open bend which could be achieved without the clasp being irreversibly deformed and mechanically damaged is given in the table.

The following materials were used to prepare the testpieces:

| Polymerizable core material | |
|---|---|
| Constituent | Proportion (wt. %) |
| Bis-GMA | 24.5 |
| Triethylene glycol dimethacrylate (TEGDMA) | 6.2 |
| Urethane dimethacrylate (UDMA) | <1.0 |
| Decane methylene glycol dimethacrylate | <1.0 |
| Highly dispersed silicon dioxide | 3.5 |

| -continued | |
|---|---|
| Polymerizable core material | |
| Constituent | Proportion (wt. %) |
| Glass fibres, silanized | 65.0 |
| Catalysts and stabilizers | <0.6 |

| Veneering material (with organic filler) | |
|---|---|
| Constituent | Proportion (wt. %) |
| Powder component | |
| PMMA | >98.0 |
| Benzoyl peroxide, pigments | <2.0 |
| Liquid component | |
| Methyl methacrylate | 66.5 |
| Ethylene glycol dimethacrylate | 33.0 |
| Diethanol-p-toluidine | 0.5 |

Powder component and liquid component were mixed together in a ratio of 2.5:1. After the polymerization, the PMMA particles of the powder component were visible in the photomicrograph of the cured material as a filler, but had no influence on the modulus of elasticity or the rigidity. The powder component acts as a non-reinforcing filler.

| Veneering material with inorganic filler | |
|---|---|
| Constituents | Proportion (wt. %) |
| Bis-GMA | 9.0 |
| Urethane dimethacrylate | 9.3 |
| Decane methylene glycol dimethacrylate | 4.8 |
| Highly dispersed silicon dioxide | 11.8 |
| Barium glass filler, silanized | 46.2 |
| Mixed oxide, silanized | 12.2 |
| Catalysts and stabilizers | <1.0 |
| Pigments | 0.1 |

TABLE 1

Measurement of the material values (testpieces)

| Material | Bending modulus of elasticity [GPa] | Max. elongation [%] | Flexibility[1] [$10^{-3} \cdot GPa^{-1}$] | Open (Upward) bend [mm] |
|---|---|---|---|---|
| Core material | 36 | 2.3 | 0.64 | 2.0 |
| Veneering material (inorg. filler) | 10 | 1.8 | 1.80 | n.m. |
| Veneering material (org. filler) | 2 | 3.5 | 17.50 | n.m. |
| Co/Cr alloy[2] | 218 | 0.25 | 0.01 | 0.2 |
| Au-cast[3] | 98 | 0.36 | 0.04 | 0.3 |
| Au-hardened[4] | 103 | 0.57 | 0.06 | 0.6 |
| Acetal resin | 3 | 2.3 | 7.67 | 1.8 |
| Core material (0.75 mm) veneered | 16 | 2.3 | 1.44 | 1.7 |

TABLE 1-continued

Measurement of the material values (testpieces)

| Material | Bending modulus of elasticity [GPa] | Max. elongation [%] | Flexibility[1] [$10^{-3} \cdot GPa^{-1}$] | Open (Upward) bend [mm] |
|---|---|---|---|---|
| on both sides (2 × 0.15 mm) (inorg. filler) | | | | |
| Core material (0.75 mm) veneered on both sides (2 × 0.15 mm) (org. filler) | 13 | 3.1 | 2.38 | 2.4 |

[1] maximum elongation in %/bending modulus of elasticity in GPa
[2]–[4] materials of customary dental quality were used
n.m. not measured

The invention claimed is:

1. Removable dental prosthesis, comprising at least one metal-free clasp-shaped anchoring element made of plastic material with a bending modulus of elasticity of at least 10 GPa, a maximum elongation of at least 0.8%, and which comprises a curable core material and a curable veneering material, wherein the core material contains a polymeric matrix material, into which a fibrous filler core material is embedded.

2. Dental prosthesis according to claim 1, wherein the plastic material has a bending modulus of elasticity of 10 to 80 GPa and a maximum elongation of 0.8 to 4%.

3. Dental prosthesis according to claim 1, wherein the bending modulus of elasticity and maximum elongation are in such a ratio to each other that the quotient of maximum elongation in % and bending modulus of elasticity in GPa is in the region of $0.4 \times 10^{-3}$ to $15 \times 10^{-3}$ $GPa^{-1}$.

4. Dental prosthesis according to claim 1, wherein the core material has a bending modulus of elasticity of more than 20 GPa and a maximum elongation of more than 1%.

5. Dental prosthesis according to claim 1, wherein the core material contains 43 to 70 wt.-% fibrous filler.

6. Dental prosthesis according to claim 1, wherein the polymeric matrix material containing fibrous filler is veneered with a polymer veneering material without fibrous filler.

7. Dental prosthesis according to claim 6, wherein the veneering material has a bending modulus of elasticity of 2 to 15 GPa and a maximum elongation of more than 1%.

8. Dental prosthesis according to claim 6, wherein the veneering material contains no inorganic filler.

9. Dental prosthesis according to claim 6, wherein the veneering material contains organic filler.

10. Kit for the preparation of a dental prosthesis comprising at least one metal-free clasp-shaped anchoring element made of plastic material with a bending modulus of elasticity of at least 10 GPa, a maximum elongation of at least 0.8%, and which comprises a curable core material and a curable veneering material, wherein the curable core material contains

| 25 to 52 wt. % | polymerizable binding agent, |
|---|---|
| 43 to 70 wt. % | fibrous filler, |
| 3 to 8 wt. % | particulate filler, |
| <2.5 wt. % | initiator for radical polymerization, |
| <2.5 wt. % | stabilizer, and |
| <0.3 wt. % | one or more pigments. |

11. Kit for the preparation of a dental prosthesis comprising at least one metal-free clasp-shaped anchoring element made of plastic material with a bending modulus of elasticity of at least 10 GPa, a maximum elongation of at least 0.8%, and which comprises a curable core material and a curable veneering material, wherein the veneering material contains

| 50 to 80 wt. % | organic filler, |
|---|---|
| 20 to 50 wt. % | polymerizable binding agent, |
| <2 wt. % | initiator for radical polymerization and |
| 0-1 wt. % | accelerator. |

12. Kit for the preparation of a dental prosthesis comprising at least one metal-free clasp-shaped anchoring element made of plastic material with a bending modulus of elasticity of at least 10 GPa, a maximum elongation of at least 0.8%, and which comprises a curable core material and a curable veneering material, wherein the veneering material comprises at least one solid component and at least one liquid component, the solid component containing the organic filler and the initiator, and the liquid component containing the binding agent and optionally, the activator.

13. Kit for the preparation of a dental prosthesis comprising at least one metal-free clasp-shaped anchoring element made of plastic material with a bending modulus of elasticity of at least 10 GPa, a maximum elongation of at least 0.8%, and which comprises a curable core material and a curable veneering material, wherein the kit contains 1 to 5 different core materials and/or 1 to 5 different veneering materials.

14. Process for the preparation of dental prostheses with metal-free anchoring elements, wherein a prosthesis base is provided with anchoring elements made of a core material, the anchoring elements are then veneered with a veneering material, and core and veneering material are cured simultaneously or successively.

15. Removable dental prosthesis, comprising at least one metal-free clasp-shaped anchoring element made of plastic material with a bending modulus of elasticity of at least 10 GPa, a maximum elongation of at least 0.8%, and which comprises a curable core material and a curable veneering material, wherein the metal-free clasp-shaped anchoring element has a maximum cross-section of 1 mm and a minimum cross-section of 0.6 mm, in the tooth horizontal direction.

16. Removable dental prosthesis, comprising at least one metal-free clasp-shaped anchoring element made of plastic material with a bending modulus of elasticity of at least 10 CPa, a maximum elongation of at least 0.8%, and which comprises a curable core material and a curable veneering material, wherein the metal-free clasp-shaped anchoring element has a cross-section in the tooth vertical direction of 1 to 2 mm.

17. Removable dental prosthesis, comprising at least one metal-free clasp-shaped anchoring element made of plastic material with a bending modulus of elasticity of at least 10 GPa, a maximum elongation of at least 0.8%, and which comprises a curable core material and a curable veneering material, wherein the core material contains 43 to 70 wt.-% fibrous filler.

* * * * *